(12) United States Patent
Durlak

(10) Patent No.: US 7,474,913 B2
(45) Date of Patent: Jan. 6, 2009

(54) METHOD FOR MEDICAL IMAGING

(75) Inventor: Peter Durlak, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 394 days.

(21) Appl. No.: 11/165,099

(22) Filed: Jun. 23, 2005

(65) Prior Publication Data

US 2005/0288578 A1 Dec. 29, 2005

(30) Foreign Application Priority Data

Jun. 25, 2004 (DE) .................... 10 2004 030 836

(51) Int. Cl.
*A61B 6/00* (2006.01)
(52) U.S. Cl. .................. 600/428; 600/424; 382/128
(58) Field of Classification Search ................ 600/463, 600/466, 428, 424; 606/130; 128/916; 345/7–9; 382/128, 132
See application file for complete search history.

(56) References Cited

U.S. PATENT DOCUMENTS

| 5,871,013 | A | 2/1999 | Wainer et al. | |
|---|---|---|---|---|
| 5,924,989 | A | 7/1999 | Polz | |
| 6,368,285 | B1 | 4/2002 | Osadchy et al. | |
| 6,389,104 | B1 * | 5/2002 | Bani-Hashemi et al. .. | 378/98.12 |
| 6,473,635 | B1 * | 10/2002 | Rasche ..................... | 600/428 |
| 6,556,695 | B1 | 4/2003 | Packer et al. | |
| 6,923,768 | B2 * | 8/2005 | Camus et al. ............. | 600/463 |
| 2003/0114749 | A1 | 6/2003 | Rahn | |
| 2003/0158477 | A1 | 8/2003 | Panescu | |
| 2004/0077942 | A1 * | 4/2004 | Hall et al. .................. | 600/428 |
| 2004/0097805 | A1 | 5/2004 | Verard et al. | |
| 2006/0173287 | A1 * | 8/2006 | Sabczynski et al. ........ | 600/424 |

FOREIGN PATENT DOCUMENTS

| DE | 196 08 971 A1 | 10/1996 |
|---|---|---|
| DE | 196 21 540 A1 | 1/1997 |
| DE | 101 57 965 A1 | 6/2003 |
| EP | 0 930 046 A2 | 7/1999 |
| EP | 1 442 707 A2 | 8/2004 |
| WO | WO 02/082375 A2 | 10/2002 |

* cited by examiner

*Primary Examiner*—Eric F Winakur
*Assistant Examiner*—Lawrence N Laryea

(57) ABSTRACT

A method for medical imaging is provided, wherein a current position of a medical instrument inserted into a moving examination area of a patient is displayed. The medical instrument is displayed within a reconstructed three-dimensional image of the moving examination area based on position data of the instrument registered with a coordinate system of the reconstructed three-dimensional image. The reconstructed three-dimensional image is a simulation of the moving examination area using a pre-insertion 3D image of the examination area correlated with pre-insertion ECG data of the patient. A display of the reconstructed three-dimensional image is triggered by current ECG data of the patient.

8 Claims, 1 Drawing Sheet

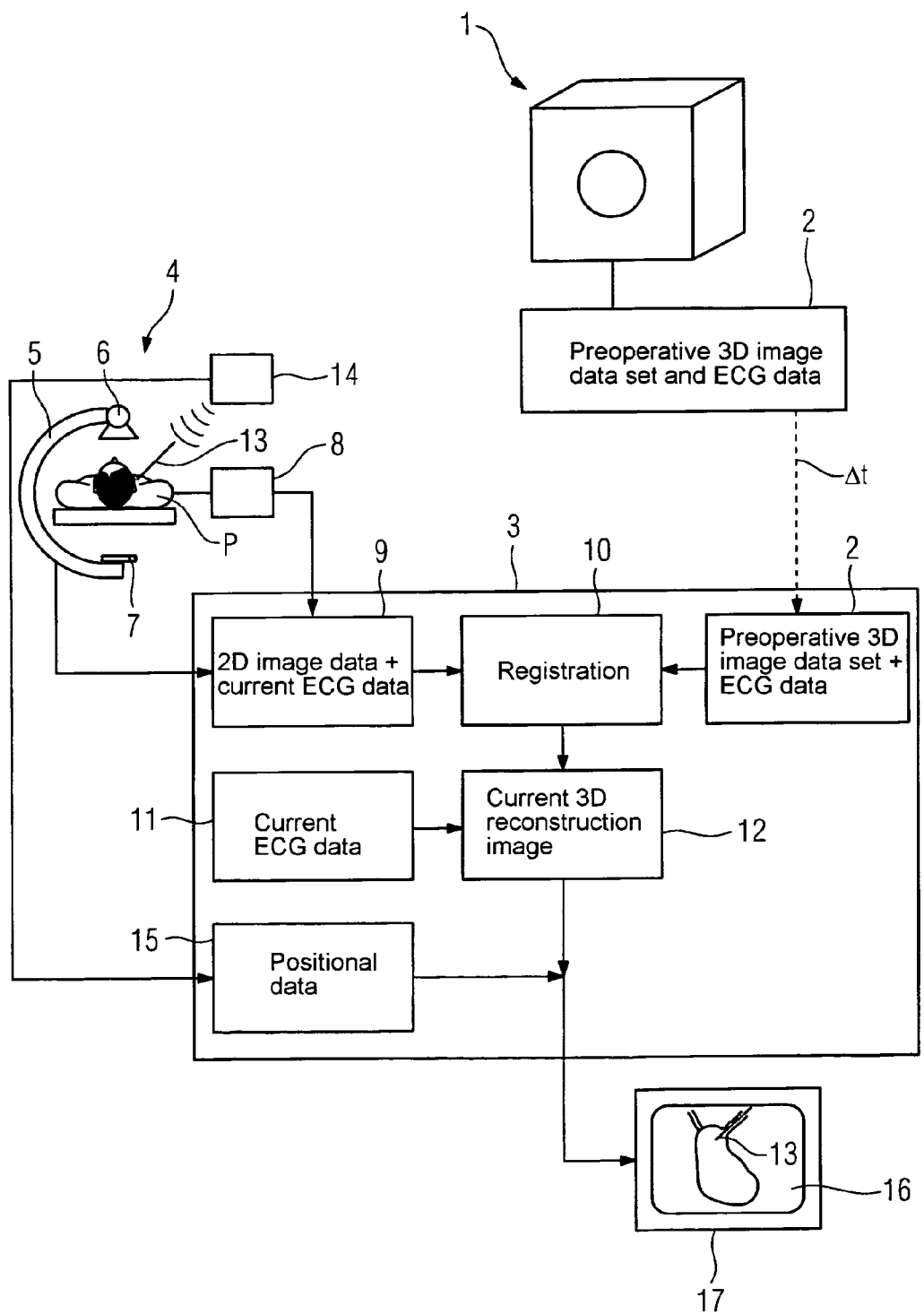

METHOD FOR MEDICAL IMAGING

CROSS REFERENCE TO RELATED APPLICATIONS

This application claims priority to the German application 10 2004 030 836.5, filed Jun. 25, 2004 which is incorporated by reference herein in its entirety.

FIELD OF INVENTION

The invention relates to a method for image presentation of a medical instrument introduced into a rhythmically or arrhythmically moving examination region of a patient, in particular a catheter.

BACKGROUND OF INVENTION

Within the scope of minimally invasive intervention actions, in which for example catheters are inserted into hollow spaces, the coronary blood vessels for example, the optical presentation of the moving instrument plays a central role in relation to the examination region in enabling the physician to navigate the instrument which is no longer visible to him after introducing it into the patient. To this end, a method is known whereby an X-ray fluoroscopy device is used to continuously record and output two-dimensional X-ray images which the physician uses for navigation purposes. The navigation using these 2D images is difficult on account of the lack of depth information or spatial information, and in addition the stress on the patient as a result of the continuous radiation image recording during the intervention is relatively high.

SUMMARY OF INVENTION

An object of the invention is therefore to set down a method which makes possible an informative image presentation of the catheter whilst simultaneously subjecting the patient to minimum radiation exposure.

This object is achieved by the claims.

In order to solve this problem, the following steps are provided according to the invention in respect of a method of the type described at the beginning:

- use of a preoperatively recorded 3D image data set of the examination region with associated ECG data for phase-related and time-related resolution of the image data for producing a 3D reconstruction image of the moving examination region,
- recording simply of one current 2D fluoroscopic image of the examination region and acquisition of the ECG data relating to the 2D fluoroscopic image,
- registration of the 3D image data set with the 2D fluoroscopic image, using the ECG data in order to enable a locationally correct presentation of the 3D reconstruction image, whereby

- the current ECG data is continuously recorded and is used to trigger the presentation of the moving 3D reconstruction image, and
- the current positional data for the instrument takes place continuously by means of a navigation system in a coordinate system registered with the coordinate system of the 3D reconstruction image and the instrument is presented in a correct positional arrangement in the 3D reconstruction image.

The method according to the invention initially provides for the use of a preoperative, in other words recorded prior to the instrument intervention, 3D image data set with which the ECG data acquired during the recording are associated, which serve to apply a fourth dimension to the 3D data set. This preoperative image data set can have been recorded using any desired mode of image recording, for example a computer tomograph, a magnetic resonance device or an ultrasound device. It contains image data which display the moving examination object, in other words the heart for example, over a plurality of cycles. On the basis of the ECG data, it is possible for each individual image of the 3D image data set to state precisely the point in time at which the image was taken and the phase in which the examination object was when the individual image was recorded, in other words the 2D individual projection. By using this 3D image data set it is now possible to determine a moving reconstruction image which shows the moving examination object, in other words the beating heart for example, in the manner of a film. This 3D reconstruction image of the moving examination area is thereupon the spatial environment in which the instrument, in other words the catheter introduced to the heart for example, is to be superimposed precisely in respect of its location, position and orientation.

In order to be able to superimpose the instrument in the image with the appropriate level of precision, it is necessary to determine the position in which the examination region is situated during the following intervention. In order to make this possible, the method provides for simply recording a current 2D fluoroscopic image of the examination region and the associated ECG data at the time of image acquisition. The 2D fluoroscopic image is recorded in a coordinate system associated with the image recording facility, which is naturally a different one to the coordinate system in which the individual images of the 3D image data set were recorded. In the next step, the 2D fluoroscopic image is then registered with the 3D image data set, which means that a mapping specification is determined which allows the two different coordinate systems to be mapped onto one another. After the registration has taken place, it is then possible to map every point in the coordinate system in which the 3D image data set was recorded with positional accuracy onto the coordinate system of the 2D fluoroscopic image recording device. For registration purposes, according to the invention a radiation image simply needs to be recorded a single time since an exact assignment of phase and time is possible as a result of the simultaneous acquisition of the ECG data. A "2D fluoroscopic image" is understood to be an individual image recorded using an X-ray machine simply comprising a combination of radiation source and radiation detector; in the case of a biplanar machine in which two such combinations arranged at an angle of 90° with respect to one another are provided it is also possible to record two individual projections in the course of the individual beam scanning for registration purposes.

When both the coordinate systems and thus the data sets have been registered, the only further action required is to acquire the current ECG data which is exclusively responsible for triggering the 3D reconstruction image presentation. As a result of the coordinate system registration and also of the association with the ECG data, it is possible by using the current ECG data to precisely reconstruct at any time the particular 3D presentation which, in relation to phase and time, and as a result of the coordinate system registration also in relation to location, reflects the current form of the investigation region even though it does not involve current image data but data recorded preoperatively. This serves to ensure that with a minimum radiation dosage it is possible to produce a three-dimensional presentation of the heart which is correct in relation to phase, time and location, simply on the basis of current ECG data.

In addition to the current ECG data, the positional data for the medical instrument in question to be presented, which can be any desired instrument, can be continuously acquired by using a navigation system. The data acquisition takes place in a native coordinate system, the third such, which is registered with the coordinate system of the 3D reconstruction image. This in turn then allows current positional data to be mapped in the 3D reconstruction image such that the instrument can be presented precisely in respect of its location, position and orientation. The navigation system itself can be of any nature. For example, one or more signal transmitters can be provided on the instrument, a flexible catheter for example, in the area of its tip, while a plurality of receivers are positioned externally which acquire the signals and pass them to an evaluation facility which determines the current system-related positional data from them, after which the data transformation takes place as a result of the registration.

In total, the method according to the invention allows a continuous presentation of the moving examination area whilst subjecting the patient to only minimal radiation exposure and simultaneously presenting the instrument with accuracy of location in the 3D volume.

Basically it is not necessary once the registration of the 2D fluoroscopic image with the 3D image data set has taken place at the beginning to record further 2D fluoroscopic images, even though this can sometimes be advantageous at times when there is a danger of the patient moving or being moved and therefore changing the current position of the examination region, even if only slightly. In order to acquire such changes, an advantageous development of the invention makes provision whereby further 2D fluoroscopic images and the associated ECG data are intermittently recorded, and these are used for the checking the registration and the correct positional presentation of the 3D reconstruction image, and making corrections where necessary. In other words, a 2D control image is recorded from time to time, depending on which the given registration situation is checked. If the analysis yields the result that the mapping parameters found within the scope of the registration are still applicable as before, in other words the examination region has not therefore changed in respect of its location, there is no need for any correction, otherwise the analysis yields a mismatch. A renewed registration procedure serves to determine a corrected mapping specification which is subsequently used as the basis for the entire further 3D image reconstruction and the corresponding presentation on the monitor and also for superimposing the instrument in the volume. The intermittent radiation images can be recorded for example at one minute intervals, or every three or five minutes. The final time interval depends on the overall duration of the intervention. The recording time interval can advantageously be set on the user side and can thus be tailored to the current situation, and can if necessary also be changed during execution of the method according to the invention, depending on requirements.

BRIEF DESCRIPTION OF THE DRAWING

Further advantages, features and details of the invention are set down in the embodiment described in the following and also with reference to the drawing.

DETAILED DESCRIPTION OF INVENTION

The drawing on the one hand shows a first mode of examination 1, a magnetic resonance imaging machine in the example illustrated, which is used for recording a preoperative 3D image data set along with the associated ECG data which are derived from an acquisition unit not shown in detail, which is represented in the field labeled 2.

This preoperative 3D image data set and the associated ECG data are passed at some later point in time ($\Delta t$) to a control and processing unit 3 of a medical examination device 4 according to the invention, here taking the form of a C-arm X-ray device 5 where they are stored. The C-arm X-ray device 5 comprises a radiation source 6 and a radiation detector 7 in the known manner, which is used for recording a 2D fluoroscopic image. This image data is likewise passed to the control unit 3. The ECG is acquired in parallel to the 2D image recording by way of an ECG acquisition unit 8. The ECG data is then associated with the 2D image data or rather the precise time of acquisition of the 2D image relative to the ECG is determined, with the result that it is possible to define exactly the point in time at which and the phase in which the examination region, in the example illustrated the heart, was recorded in the form of the 2D image (see field 9 in the figure).

After the 2D image recording has taken place, which occurs a single time for registration purposes, the 2D image data and the 3D image data set are registered with one another using the respective ECG data, as represented in field 10. Within the framework of registration, the coordinate systems associated with the two image recording modes 1 and 5 respectively are registered with one another in order to determine a common mapping specification. By using the registration in conjunction with acquisition of the current ECG data by way of the ECG acquisition unit 8, represented in field 11, it is then possible to reconstruct a current 3D reconstruction image from the 3D image data set which is correct in relation to phase and time, which means that at any desired point in time the heart can be represented in its actual form in the example illustrated since the current ECG data allows the use of precisely that image data from the 3D image data set for reconstruction purposes which has been recorded in relation to the same phase and at the same point in time as defined by the current ECG. This current 3D reconstruction image is given in field 12.

In order to now be able to present an introduced medical instrument 13, a flexible heart catheter for example, in the current 3D reconstruction image, the instrument 13 is acquired by way of a navigation system 14 which can be of any nature and the corresponding positional data, represented in field 15, is continuously recorded. The coordinate system of the navigation system 14 in which the positional data is recorded is registered with the coordinate system of the 3D image data set and thus by way of a corresponding mapping specification also with the current 3D reconstruction image. By using the positional data 15 it is then possible in the resulting image 16, represented on a monitor 17, on the one hand to continuously present the moving heart in its motion and simultaneously superimpose the instrument 13 in the volume image precisely in respect of its location and orientation. The physician can thus see the pulsating heart continuously in the manner of a video film, which—even though based on a preoperative 3D image data set—as a consequence of the current ECG data being continuously recorded is presented to him in its current motion and thus in the current position. The superimposition of the instrument 13 into this current presentation of motion allows the physician to navigate easily. The radiation to which the patient is subjected is reduced to a minimum.

In order to be able to acquire any possible changes in the position of the patient P during the intervention, which can occur for any manner of reasons and which change or render invalid the given registration of the 2D images recorded initially with the 3D image data set such that the current 3D reconstruction image is ultimately no longer capable of presenting the heart in its actual location, it is advantageous if a new 2D fluoroscopic image is recorded from time to time and the registration checked in field 10, and updated if necessary.

The invention claimed is:

1. A method of generating a medical image of a medical instrument inserted into a moving examination area of a patient, the method comprising:

recording a three-dimensional image data set of the examination area before inserting the medical instrument into the examination area;

assigning ECG data to the three-dimensional image data set such that the three-dimensional image data set is divided into a plurality of movement phases and corresponding time intervals;

recording a current two-dimensional fluoroscopic image of the examination area;

recording current ECG data of the patient data while recording the current two-dimensional fluoroscopic image;

registering the three-dimensional image data set with the current two-dimensional fluoroscopic image using the current ECG data of the patient; and reconstructing a three-dimensional reconstruction image of the moving examination area using the three-dimensional image data set registered with the current two-dimensional fluoroscopic image such that the three-dimensional reconstruction image corresponds to and represents the movement phases of the examination area, the three-dimensional reconstruction image having a first coordinate system, wherein the current ECG data are continuously recorded while the medical instrument is inserted into the examination area, the three-dimensional reconstruction image of the moving examination area is displayed using the current ECG data as trigger signals, current position data of the medical instrument are continuously acquired while the medical instrument is inserted into the examination area using a navigation system, the current position data having a second coordinate system registered with the first coordinate system, and the medical instrument is displayed within the display of the three-dimensional reconstruction image using the current position data, the display of the medical instrument continuously representing a current position of the medical instrument relative to the moving examination area.

2. The method according to claim 1, wherein the examination area has a periodical movement.

3. The method according to claim 1, wherein the medical instrument is a catheter.

4. The method according to claim 1, wherein the examination area includes the heart of the patient 5. The method according to claim 1, wherein the current two-dimensional fluoroscopic image is a single two-dimensional fluoroscopic image.

6. The method according to claim 1, wherein a plurality of current two-dimensional fluoroscopic images and a plurality of current ECG data of the patient data are recorded while the medical instrument is inserted into the examination area.

7. The method according to claim 6, wherein the three-dimensional reconstruction image is corrected based on the plurality of current two-dimensional fluoroscopic images and current ECG data.

8. A medical imaging device for generating a medical image of a medical instrument inserted into a moving examination area of a patient, the imaging device comprising a control unit configured to:

record a three-dimensional image data set of the examination area before the medical instrument is inserted into the examination area;

assign ECG data to the three-dimensional image data set such that the three-dimensional image data set is divided into a plurality of movement phases and corresponding time intervals;

record a current two-dimensional fluoroscopic image of the examination area;

record current ECG data of the patient data while recording the current two-dimensional fluoroscopic image;

register the three-dimensional image data set with the current two-dimensional fluoroscopic image using the current ECG data of the patient; and reconstruct a three-dimensional reconstruction image of the moving examination area using the three-dimensional image data set registered with the current two-dimensional fluoroscopic image such that the three-dimensional reconstruction image corresponds to and represents the movement phases of the examination area, the three-dimensional reconstruction image having a first coordinate system, wherein the current ECG data are continuously recorded while the medical instrument is inserted into the examination area, the three-dimensional reconstruction image of the moving examination area is displayed using the current ECG data as trigger signals, current position data of the medical instrument are continuously acquired while the medical instrument is inserted into the examination area using a navigation system, the current position data having a second coordinate system registered with the first coordinate system, and the medical instrument is displayed within the display of the three-dimensional reconstruction image using the current position data, the display of the medical instrument continuously representing a current position of the medical instrument relative to the moving examination area.

* * * * *